United States Patent
French

(10) Patent No.: US 6,330,882 B1
(45) Date of Patent: Dec. 18, 2001

(54) EMERGENCY APPARATUS FOR EVACUATING AIR FROM THE BODY CAVITY

(76) Inventor: Ronald French, 3525 Prytania St., Suite 606, New Orleans, LA (US) 70115

( * ) Notice: Subject to any disclaimer, the term of this patent is extended or adjusted under 35 U.S.C. 154(b) by 0 days.

(21) Appl. No.: 09/036,255

(22) Filed: Mar. 6, 1998

(51) Int. Cl.$^7$ .................................................. A61M 16/00
(52) U.S. Cl. ............................... 128/200.26; 128/207.16; 128/207.29
(58) Field of Search ......................... 128/200.26, 207.16, 128/207.29

(56) References Cited

U.S. PATENT DOCUMENTS

| | | | | |
|---|---|---|---|---|
| 3,307,551 | * | 3/1967 | Violet, Jr. | 128/207.29 |
| 3,511,243 | * | 5/1970 | Toy | 128/207.29 |
| 3,613,684 | * | 10/1971 | Sheridan | 604/264 |
| 4,153,058 | * | 5/1979 | Nehme | 604/167 |
| 4,440,161 | * | 4/1984 | Wadhwa | 128/207.29 |
| 4,617,929 | * | 10/1986 | Gill | 128/207.29 |
| 5,546,939 | * | 8/1996 | French | 128/207.29 |
| 5,562,677 | * | 10/1996 | Hildwein et al. | 606/108 |

* cited by examiner

Primary Examiner—Aaron J. Lewis

(74) Attorney, Agent, or Firm—Garvey, Smith, Nehrbass & Doody, LLC

(57) ABSTRACT

An apparatus for evacuating air from the body cavity of the patient during a collapsed lung condition which includes, an air delivery tube portion which is inserted through the skin and into the wall of the body cavity, the air delivery tube portion of the apparatus include a body portion, a first upper threaded end, and a bore extending through the body portion to accommodate air flow through the air delivery tube; there is also provided a trocar member, including a body portion insertable through the bore of the air delivery tube, with a pointed end partially protruding out of the second lower end of the tube for piercing the body cavity wall during insertion of a portion of the air delivery tube into the body cavity; an extender portion engageable to the first upper end of the air conveying tube after the tube has been inserted into the body cavity and the trocar member has been removed from the air delivery tube, for providing a point of delivering air flow through the air delivery tube from the body cavity of the patient; a valving member on the upper end of the extender portion for allowing one-way flow of air out of the body cavity and for preventing air returning into the body cavity as the patient inhales; a flexible, rubber-like tube insertable through the bore in the body portion in the air delivery tube, one end of the tube insertable into the body cavity, so that the air delivery tube may be removed from the body cavity and the flexible rubber-like tube allow air flow through the tube; a valving member on the outer end of the tube for allowing air flow out of the body cavity but for preventing air flow into the body cavity as the patient inhales.

15 Claims, 4 Drawing Sheets

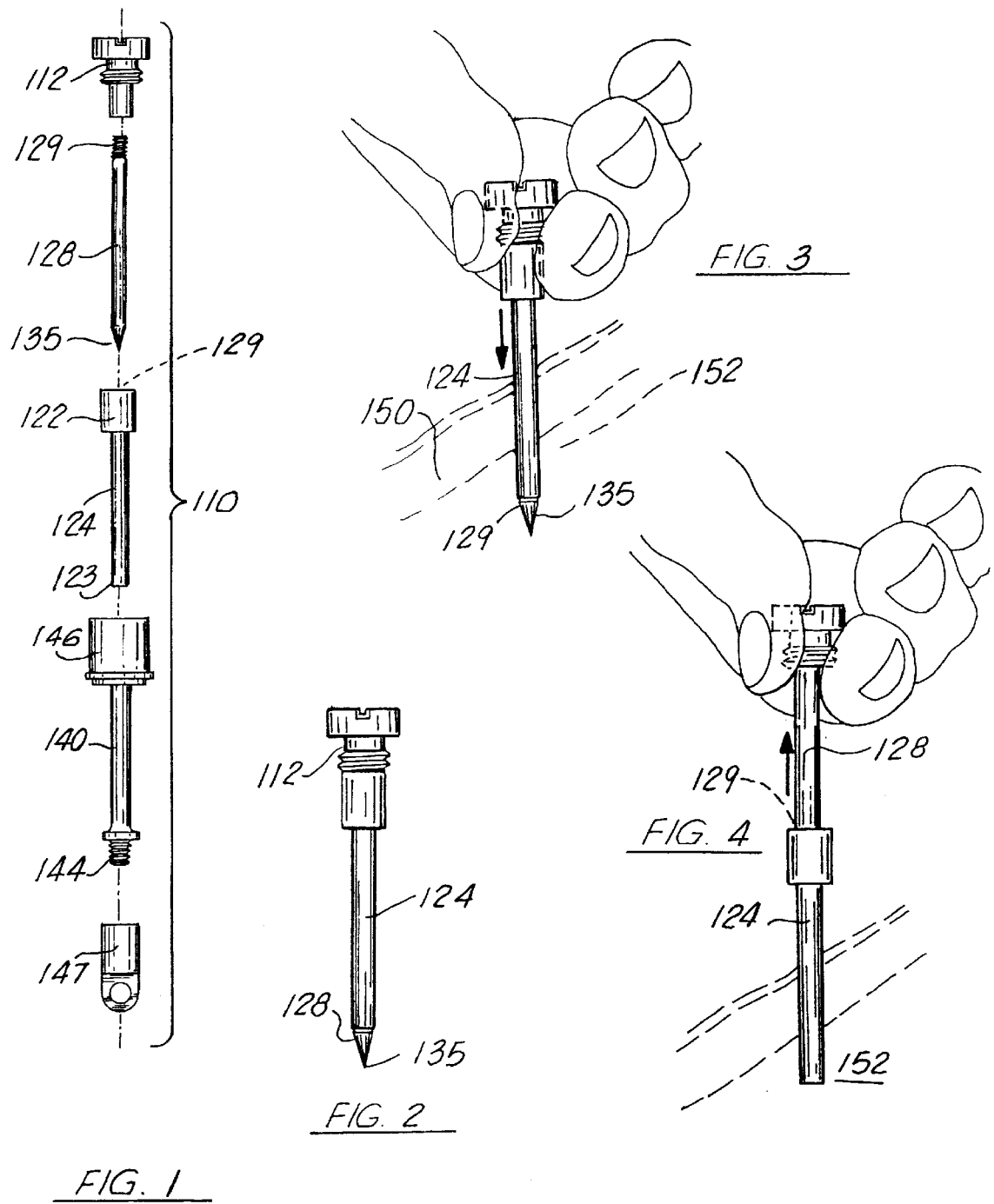

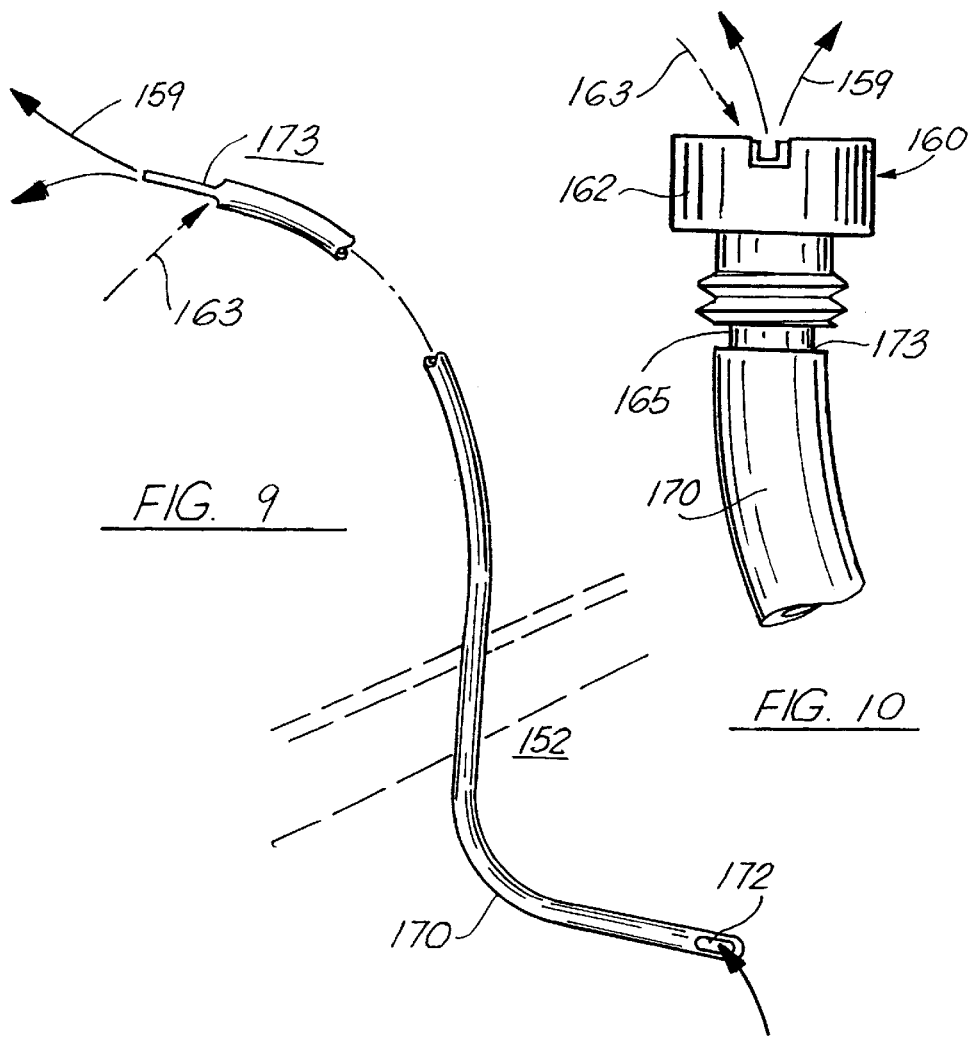
FIG. 9
FIG. 10
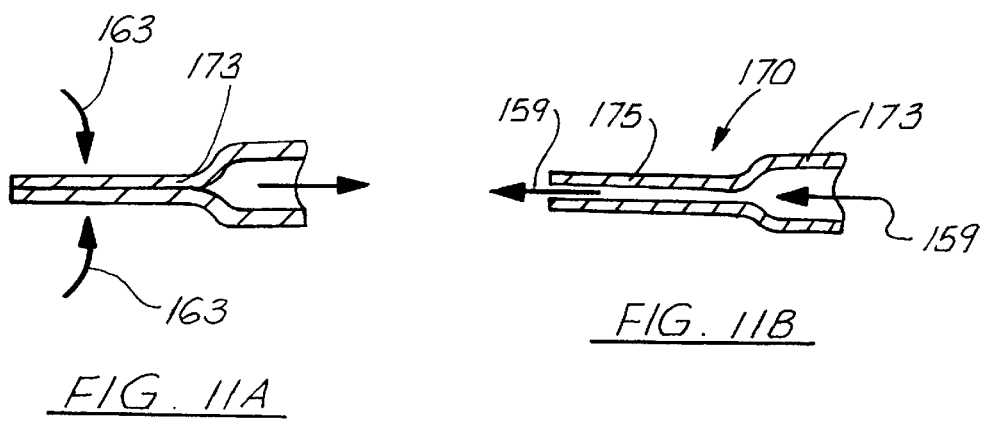
FIG. 11A
FIG. 11B

EMERGENCY APPARATUS FOR EVACUATING AIR FROM THE BODY CAVITY

CROSS-REFERENCE TO RELATED APPLICATIONS

Not applicable

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The apparatus of the present invention relates to emergency medical procedures. More particularly, the present invention relates to an apparatus that can be assembled to provide a device for establishing an air passage for evacuating air from the chest cavity of a person due to a collapsed lung condition.

2. General Background of the Invention

U.S. Pat. No. 5,546,939, entitled "Emergency Tracheostomy Apparatus" was issued to the present invention on Aug. 20, 1996, for an emergency tracheostomy apparatus. The apparatus as disclosed and claimed in that patent is utilized to perform emergency tracheostomies on patients. The present invention, is an apparatus which addresses an additional problem of air which has accumulated in the body cavity of a person due to a collapsed lung condition, and would establish an air passage for evacuating air from the chest cavity to prevent further injury to the patient.

There is an emergency medical condition which is brought about by a person who may have suffered a collapsed lung. For example, when a collapsed lung is caused by a trauma to the rib cage, not only may the lung collapse, but for example, a rib may pierce the sack surrounding the lungs, which would result in any air which is inhaled by the patient to escape into the body cavity between the exterior wall of the body cavity and the sack surrounding the lungs. If this condition is left unattended, it could result in a potentially fatal outcome. As the air accumulates in the body cavity, the air would put increased pressure on the sack surrounding the patient's heart, which due to this increased pressure, would lead if not attended to properly to heart failure. Although this type of a condition can be easily rectified in the confines of a hospital, if such a condition would occur in a setting where there is no emergency equipment to rectify the situation, death of the patient may be inevitable.

Therefore, there is a need in the medical art for a simple apparatus which can be utilized by a doctor, and carried on his or her person, so that should this emergency medical condition arise, the doctor may act quickly with the use of the apparatus and easily rectify the situation and save the life of the patient.

BRIEF SUMMARY OF THE INVENTION

The apparatus of the present invention solves the problems in the art in a simple and straightforward manner. What is provided is an apparatus for evacuating air from the body cavity of the patient during a collapsed lung condition which includes, an air delivery tube portion which is inserted through the skin and into the wall of the body cavity, the air delivery tube portion of the apparatus include a body portion, a first upper threaded end, and a bore extending through the body portion to accommodate air flow through the air delivery tube; there is also provided a trocar member, including a body portion insertable through the bore of the air delivery tube, with a pointed end partially protruding out of the second lower end of the tube for piercing the body cavity wall during insertion of a portion of the air delivery tube into the body cavity; an extender portion engageable to the first upper end of the air conveying tube after the tube has been inserted into the body cavity and the trocar member has been removed from the air delivery tube, for providing a point of delivering air flow through the air delivery tube from the body cavity of the patient; a valving member on the upper end of the extender portion for allowing one-way flow of air out of the body cavity and for preventing air returning into the body cavity as the patient inhales; a flexible, rubber-like tube insertable through the bore in the body portion in the air delivery tube, one end of the tube insertable into the body cavity, so that the air delivery tube may be removed from the body cavity and the flexible rubber-like tube allow air flow through the tube; a valving member on the outer end of the tube for allowing air flow out of the body cavity but for preventing air flow into the body cavity as the patient inhales.

Therefore, it is a principal object of the present invention to provide an apparatus for evacuating air out of the body cavity in the event that a person has a collapsed lung and air is collecting in the body cavity.

It is a further object of the present invention to provide an apparatus for evacuating air from the body cavity which utilizes a single needle puncture through the skin into the body cavity so that air can be vacated through the air delivery tube of a needle to prevent air pressure from building up within the body cavity;

It is a further object of the present invention to provide an apparatus for treating a condition known as pneumothorax, so that the air may be evacuated from the body cavity, and yet when the person attempts to breathe in order to re-inflate one's lung, a one-way valving means on the apparatus prevents air from flowing back into the body cavity during inhalation;

It is a further object of the present invention to provide an apparatus which may be utilized to evacuate air which may have collected in the body cavity due to a collapsed lung, and allow a rubber tube to be positioned so as to receive the air from the body cavity and yet include a valving means for preventing air from flowing back into the body cavity during inhalation.

It is a further object of the present invention to provide an emergency tracheostomy apparatus which can be carried in one's pocket, easily assembled for use, and easily restored for non-use by the user.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 1 is an overall exploded view of an alternate embodiment of the apparatus of the present invention.

FIG. 2 illustrates the trocar member of the apparatus of the present invention positioned within the elongated housing;

FIG. 3 illustrates the trocar member and housing of embodiment of the present invention inserted through the skin into the lung cavity;

FIG. 4 illustrates the trocar member being removed from the elongated housing remaining in the lung cavity;

FIG. 9 illustrates the air tube inserted into the lung cavity with the extender removed therefrom;

FIG. 10 shows an isolated view of a valving element secured to the outer end of the air tube used in the present invention; and FIGS. 11A and 11B illustrate views respectively of air flow through a self sealing air flow tube in the air flow tube used with the apparatus of the present invention.

DETAILED DESCRIPTION OF THE INVENTION

Figure 5:
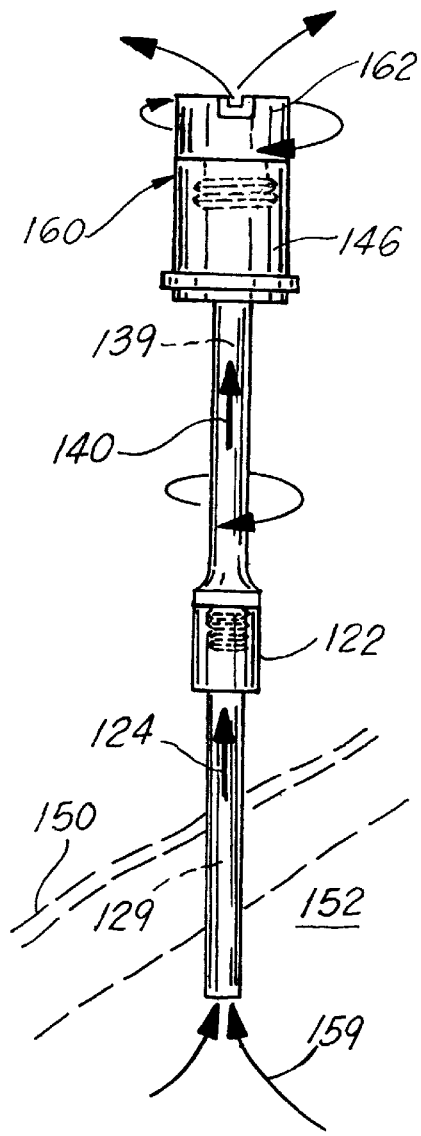
FIG. 5 illustrates the extender portion secured to the outer end of the elongated housing as it resides in the lung cavity.

FIGS. 1–11B illustrate the preferred embodiment of the emergency tracheostomy apparatus, as the apparatus would be utilized with a condition known as pneumothorax caused by a collapsed lung condition.

Prior to a discussion of the Figures, in this particular embodiment of the apparatus, the apparatus is being utilized as a system for treating a specific condition which is caused by a collapsed lung. As background, when a lung undergoes collapse, i.e. is unable to inflate with air drawn in by the movement of the diaphragm, for example, caused by a broken rib, often times the sack surrounding the lung cavity is also punctured. Therefore, as the patient attempts to inhale, air escapes out of the lung cavity and accumulates between the lung sack and the patient's torso. Such a condition can be fatal, since as more air is drawn into the cavity, it forces the pressure up against the lungs and ultimately against the heart which would result in heart failure and immediate death to the patient. Therefore, such a condition should be remedied as quickly as possible and could be done so with the alternate embodiment of the apparatus as will be discussed below.

Turning now to FIG. 1, the exploded view of the apparatus includes the apparatus 110 comprised of an upper removable cap portion 112 threadable to a trocar member 128 having an upper threadable portion 129 and a lower pointed end 135. The trocar member 128 would be insertable into an elongated housing 124 having an upper enlarged housing portion 122 and a lower end 123. The trocar member 128 secured into the housing 124 would then be inserted into an extender member 140 having an enlarged upper end 146 and a lower threaded end 144, with the threaded end 144 threadable onto a lower cap member 147. In the exploded view as seen in FIG. 1, this assembly would be put together into a full assembly when the apparatus is not in use and could be carried around in that manner. The upper end cap 112 and lower end cap member 147 when in place, would seal both ends of the apparatus when not in use, so that it may be portable and the components, as described above, would be maintained sterile. In the event an emergency would occur and the apparatus would have to be utilized to rectify an emergency condition, as was stated earlier, the cap members 112, 147 would be removed so that the apparatus could then be disassembled, and as seen in FIGS. 2–11B, would be reassembled for emergency use.

As seen in FIG. 2, the trocar member 128 is inserted into a bore 129 in the elongated housing 124 with the threadable end 112 threaded there onto and point 135 extending out of the housing 124. Reference is now made to FIG. 3 where it is seen that the trocar member 128 within housing 124 is being inserted through the outer skin 150 of a patient and into the cavity 152 which could be defined as that area between the skin 150 of the patient and the inner lung sack wherein air would be accumulating due to intake of air by the patient and the air flowing out of the punctured sack into the area 152 which air must be vacated as soon as possible. Therefore, after the point 135 of the trocar member 128 has punctured the skin 150, reference is made to FIG. 4 where the trocar member 128 is removed from the housing 124 and upon removing the trocar 128, air is then able to flow out of the bore in housing 124 to relieve the pressure within space 152.

One of the shortcomings in this particular basic unit as seen in FIGS. 1–4 is the fact that should the patient attempt to continue to breathe, because of the clear air passageway through housing 124, air would tend to enter housing 124 into the cavity 152 when a patient inhales. Therefore, reference is made to FIGS. 5–6A where again there is illustrated the housing 124 with the extender 140 threadably engaged to the upper end 122 of housing 124 and with a modified cap 160 threadably secured to the upper end 146 of extender 140. As illustrated in FIG. 5, the modified cap 160, which is seen in cross section view in FIGS. 6A and 6B, and will be discussed further, would include a top portion 162 which would be engaged onto the cap 160 when the cap 160 is in its storage mode i.e. when it is being carried around and not in use. The reason that protection cap 162 is in place upon modified top 160 is that the modified top 160 includes a valving element 164 which should be protected while the apparatus is not in use.

Figure 6B:
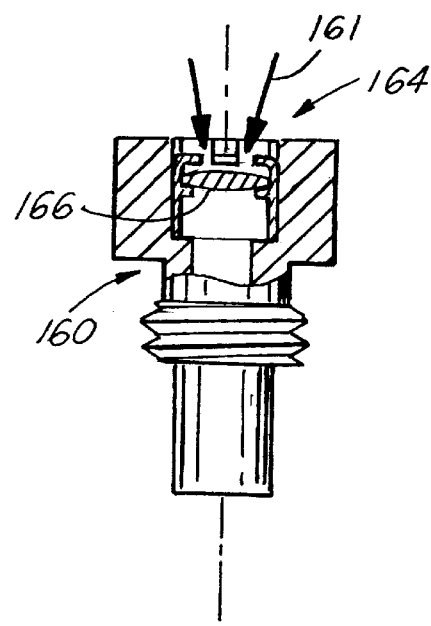
FIGS. 6A and 6B illustrate the air flow through the modified top portion of the extender of the alternate embodiment of the present invention.
Figure 6A:
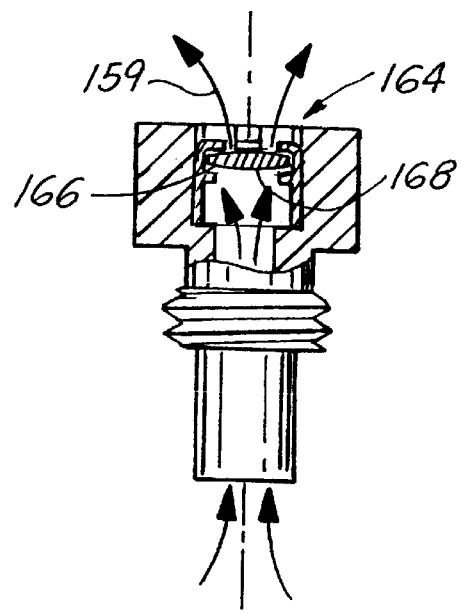
Figure 7:
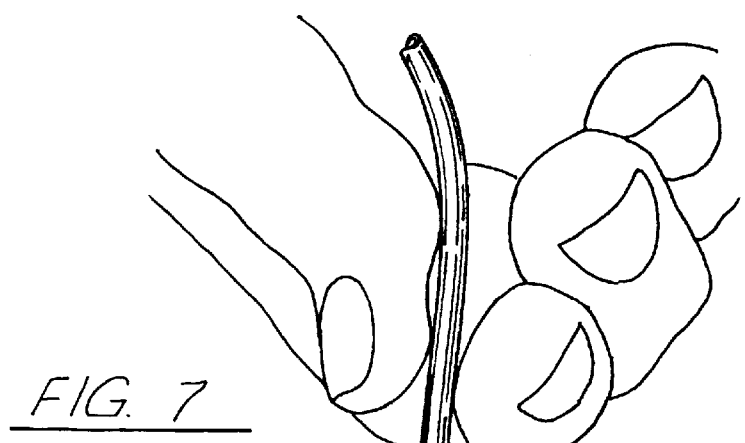
FIG. 7 illustrates an air delivery tube being inserted into the elongated housing in the alternate embodiment of the present invention.

Therefore, in FIG. 5, once the elongated housing is seen inserted through the skin 150 and air (arrows 159) is moving upward through the bore 129 in member 124 and then through the elongated opening 139 in extender 140, it would be unable to flow out of cap 160 due to the protector 162 thereon. Therefore, the protector 162 is removed from cap 160, as seen in FIG. 6A, and the one-way valving element 164 allows the air to flow in the direction of arrows 159 and out of the apparatus to relieve the pressure in the cavity 152. It should be known that the valving element 164 is a rather small valving element being a one-way valve having a wafer member 166 which when air under pressure encounters it on its underside 168, the wafer 166 allows the air to flow through the valving element 164. However, as seen in FIG. 6B, should air attempt to return for example in the direction of 161, the wafer member 166 will move into sealing engagement in the valving element 164 and will not allow air to return. Therefore, this would prevent air from moving back into the cavity 152 through the apparatus, when a patient inhaled, as is illustrated in the Figures. Although it is illustrated in FIG. 5 that the cap member 160 is threadably engaged to the extender 140 which is then further threadably engaged to the air delivery tube 124, it is foreseen that in a particular embodiment, one may not choose to use the extender 140, but may choose to modify cap 160 and have it threaded directly onto the upper end of the air delivery tube 124. However, the preferred embodiment as illustrated in FIG. 5 illustrates the cap 160 threadably engaged to extender 140 which is also then threadably engaged to air delivery tube 124 which has been thrust through the skin 150 into the body cavity 124 and would accommodate air flow therethrough after cap 162 has been removed, as illustrated in FIG. 6A.

Figure 8:
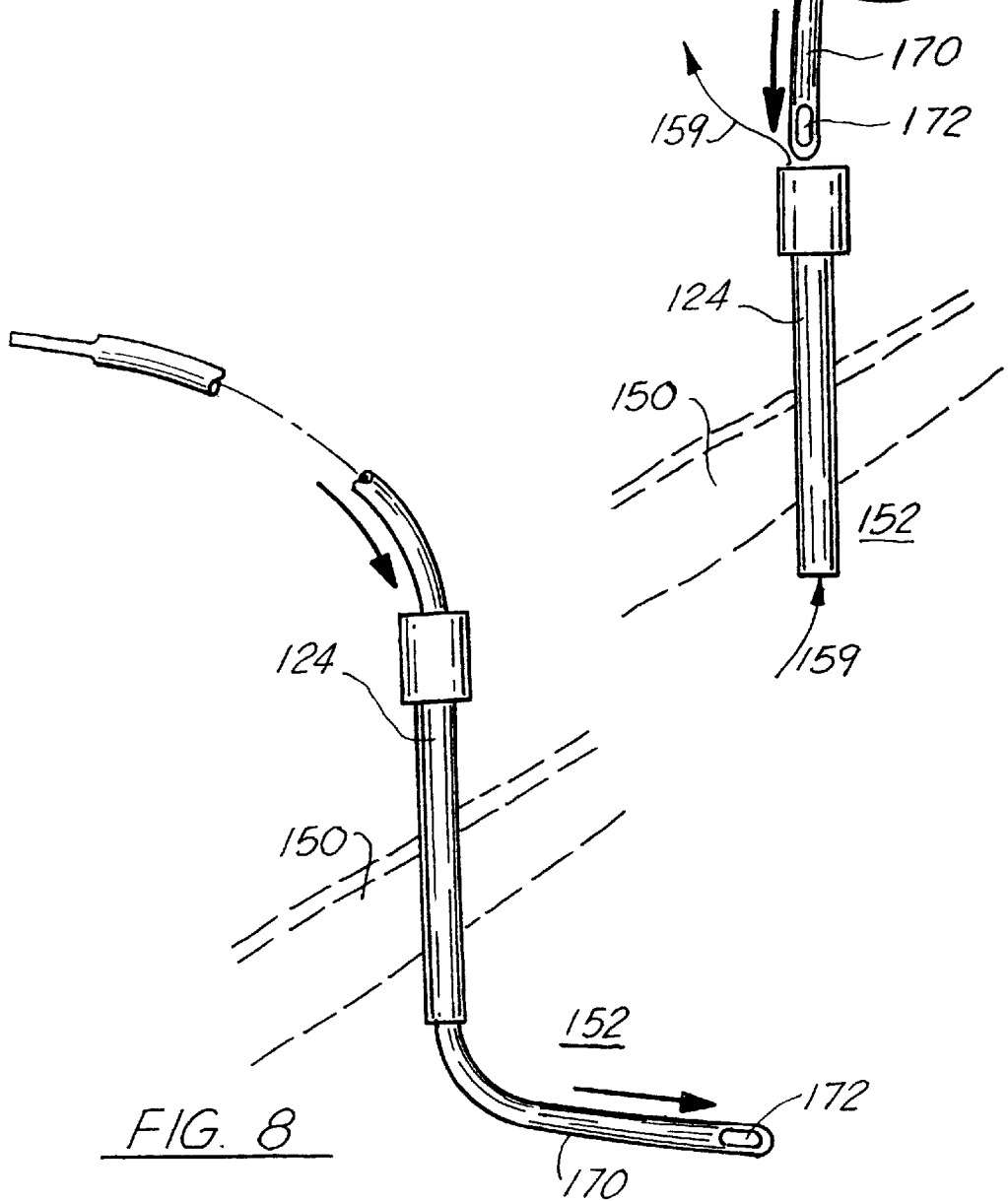
FIG. 8 illustrates the air tube having been inserted into the lung cavity for allowing flow of air therethrough in the ultimate embodiment of the present invention.

An additional feature which can be utilized in the apparatus is seen in FIGS. 7–11B. In this particular embodiment of the apparatus, it is seen again for example in FIGS. 7 and 8, that the housing 124 again is inserted in through the skin 150 of the patient and the lower end of which is again within cavity 152 for allowing the air to flow out of cavity 152 through the apparatus in the direction of arrows 159. In this particular embodiment, rather than utilize the cap 160 with the valving element 164 therein, one could use an air tube 170. Air tube 170 is of the type that is a flexible rubber-like tube having an airflow bore 172 through its length. Air tube 170 would be inserted through the bore 129 in housing 124 and would be threaded into the cavity 152 as seen in FIG. 8. At this point, reference is made to FIG. 9 where after tube 170 has been inserted through the elongated housing 124, the elongated housing 124 can then be removed from the skin and as seen in FIG. 9, the only thing remaining into the patient's cavity is tube 170.

This is a critical feature in view of the fact that under current FDA rules, one cannot maintain a metal item such as housing 124 within the body cavity and therefore, in this particular embodiment, the elongated housing 124 could be withdrawn and the rubber medical tube 170 is the only thing within the cavity 152, the second end 173 of which is extending out of the body cavity 152 for allowing air to flow therethrough. However, even with the tube 170 being utilized, one may encounter the problem of the fact that if the tube 170 is simply open-ended on its outer end 173, air shown by air 159 would flow out of the cavity but again, if the patient should inhale, air may return in the direction of arrows 163 into the cavity. Therefore, one must then have a means for preventing the air from returning in the direction of arrow 163 as seen in FIG. 9. The first means may be the modified or the valving cap 160 which was discussed in relation to FIGS. 6A and 6B. This cap 160 could have a lower end 165 which would simply be inserted into the opening 173 of the upper end of tube 170 and would therefore, when the protector cap 162 is removed, the cap 160 would operate in the same manner as was discussed in 6A and 6B, that is, allowing air to flow out of the tube in the direction of arrows 159 but disallowing any return of air in the direction of arrow 163.

Turning now to FIGS. 11A and 11B, there is yet another means which is more simplified than the cap 160 for disallowing air to travel back within tube 170. As seen in FIG. 11A, the outer end 173 of tube 170 is provided with a self-sealing element 175 that is simply a provision that the end of tube 170 is normally in the sealed position as seen in FIG. 11A and would never allow air to enter in the direction of arrows 163. However, when air would be flowing from the cavity 152 under pressure, because of the flexibility of the sealing elements of end 173, the air would create an opening 181 in the end 173 of the flow tube 170 and air would then flow out of the body cavity in the direction of arrows 159. In this particular embodiment then, there would simply be the air tube 170 as seen in FIG. 9 in the body cavity with the self-sealing end 173 as seen in FIGS. 11A and 11B on the end of the tube 170, and thus that would eliminate the need for the modified cap member 160 and would be within the FDA restrictions for maintaining a tube in a body cavity 152 as illustrated. Therefore, emergency efforts could be conducted and the airflow tube could be maintained to correct any imbalance in pressure within cavity 152 until the proper medical treatment arrived.

The foregoing embodiments are presented by way of example only; the scope of the present invention is to be limited only by the following claims.

I claim:

1. An apparatus for evacuating air from a body cavity, comprising:
    a) an air delivery tube insertable through the skin into the body cavity, having a body portion, a first upper end, a second end insertable through the skin into the body cavity, and a bore extending throughout the body portion to accommodate air flow through the air delivery tube out of the body cavity; and
    b) flexible tubing having a first end insertable through the bore in the air delivery tube into the body cavity, and a valve on a second end of the flexible tubing to allow the air delivery tube to be removed from the body cavity and the tubing remain to continue to evacuate air from the body cavity.

2. The apparatus in claim 1, further comprising removable cap members for sealing the apparatus on the upper and lower ends to maintain the apparatus sterile and portable while the apparatus is not in use.

3. The apparatus in claim 1, further comprising a trocar member including a body portion insertable through the bore of the air delivery tube, with a first pointed end partially protruding out of the second lower end of the tube for defining a means to pierce a patient's tracheal wall during insertion of a portion of the air delivery tube into a patient's trachea and a second upper end having an outer threaded wall protruding from the first end of the air delivery tube.

4. The apparatus in claim 1, further comprising an extender portion having an elongated body portion, with a diameter sufficient to accommodate the air delivery tube housing the trocar therein, and an upper body portion of sufficient diameter to threadably engage the upper threaded wall of the trocar member.

5. An apparatus for evacuating air from a body cavity, comprising:
    a) an air delivery tube, having a body portion, a first end, a second end, and a bore extending throughout the body portion to accommodate air flow through the air delivery tube;
    b) a trocar member including a body portion insertable through the bore of the air delivery tube, with a pointed end partially protruding out of the second lower end of the air delivery tube;
    c) extender means engageable to a first upper end of the air delivery tube defining a means to provide air flow through the air delivery tube into a body cavity of a patient; and
    d) a sealable valving member on the extender means to provide for air flow out of the body cavity, but to disallow flow of air into the body cavity through the air delivery tube.

6. The apparatus in claim 5, further comprising removable cap members for sealing the apparatus on the upper and lower ends to maintain the apparatus sterile and portable while the apparatus is not in use.

7. The apparatus in claim 5, further comprising a threaded portion on an upper end of the air delivery tube for threadably engaging the extender means thereto for air delivery.

8. The apparatus in claim 5, wherein the trocar member is removable from the air delivery tube before the extender means is threadably engaged to the air delivery tube.

9. The apparatus in claim 5, wherein the extender means further comprises a bore through a body portion of sufficient length and diameter so as to accommodate the air delivery tube within the bore of the extender means when the air delivery tube is not in use.

10. The apparatus in claim 5, wherein the trocar member is positioned within the air delivery tube when the tube is housed within the extender means, and a top portion of the trocar member is threadably engaged to a top portion of the extender means during non-use.

11. The apparatus in claim 5, further comprising a length of flexible tubing threadable through the bore of the air delivery tube and into the body cavity, so that the air delivery tube may be removed from the body cavity and air flow out of the body cavity continues through the flexible tubing.

12. The apparatus in claim 11, further comprising a valving member on the end of the flexible tubing to control air flow only one way out of the body cavity.

13. An apparatus for evacuating air from a person's body cavity which may have collected due to a collapsed lung condition, the apparatus comprising:

a) an air delivery tube, having a body portion, a first end, a second end, and a bore extending throughout the body portion to accommodate air flow through the air delivery tube;

b) a trocar member including a body portion insertable through the bore of the air delivery tube, with a pointed end partially protruding out of the second lower end of the tube for defining a means to puncture a wall of the body cavity during insertion of a portion of the air delivery tube into the body cavity;

c) an extender portion engageable to a first upper end of the air delivery tube after the tube has been inserted into the body cavity, and the trocar member has been removed from the air delivery tube, for defining a means of providing air flow through the air delivery tube out of a patient's body cavity;

d) a valving member on the end of the extender portion for providing one way flow of air out of the body cavity and preventing air flow into the body cavity through the air delivery tube; and e) cap means on the upper and lower ends of the apparatus for maintaining the apparatus sealed from the outside so as to maintain the apparatus sterile and portable when not in use.

14. The apparatus in claim 13, further comprising a flexible tube insertable through the bore in the air delivery tube into the body cavity, so that the air delivery tube may be removed from the body cavity and the tube remain to continue to evacuate air from the body cavity.

15. The apparatus in claim 14, wherein the flexible tube further comprises a valving member on its end to allow air to flow out of the body cavity but to prevent air from flowing into the body cavity through the tube.

\* \* \* \* \*